United States Patent
Gatzemeyer

(10) Patent No.: US 9,125,484 B2
(45) Date of Patent: Sep. 8, 2015

(54) ACTIVE DELIVERY ORAL CARE IMPLEMENT

(75) Inventor: John Gatzemeyer, Hillsborough, NJ (US)

(73) Assignee: COLGATE-PALMOLIVE COMPANY, New York, NY (US)

(*) Notice: Subject to any disclaimer, the term of this patent is extended or adjusted under 35 U.S.C. 154(b) by 1187 days.

(21) Appl. No.: 12/145,775

(22) Filed: Jun. 25, 2008

(65) Prior Publication Data
US 2009/0311294 A1    Dec. 17, 2009

(51) Int. Cl.
| | |
|---|---|
| *A46B 11/00* | (2006.01) |
| *A61K 8/22* | (2006.01) |
| *A61K 8/38* | (2006.01) |
| *A61K 8/41* | (2006.01) |
| *A61K 8/81* | (2006.01) |
| *A61K 8/86* | (2006.01) |
| *A61Q 11/00* | (2006.01) |

(52) U.S. Cl.
CPC ......... *A46B 11/0058* (2013.01); *A46B 11/0065* (2013.01); *A61K 8/22* (2013.01); *A61K 8/38* (2013.01); *A61K 8/416* (2013.01); *A61K 8/8147* (2013.01); *A61K 8/86* (2013.01); *A61Q 11/00* (2013.01); *A46B 2200/1066* (2013.01); *A61K 2800/87* (2013.01)

(58) Field of Classification Search
USPC ........................................................ 424/401
See application file for complete search history.

(56) References Cited

U.S. PATENT DOCUMENTS

| | | |
|---|---|---|
| 3,389,468 A | 6/1968 | Lewis et al. |
| 4,519,751 A | 5/1985 | Beckman et al. |
| 5,403,105 A | 4/1995 | Jameson |
| 5,476,333 A | 12/1995 | Matthews |
| 5,476,384 A | 12/1995 | Giuliani et al. |
| 5,642,994 A | 7/1997 | Chipian et al. |
| 5,785,956 A | 7/1998 | Sullivan et al. |
| 6,164,967 A | 12/2000 | Sale et al. |
| 6,648,641 B1 | 11/2003 | Viltro et al. |
| 2001/0002228 A1 | 5/2001 | Owens |
| 2002/0090252 A1 | 7/2002 | Hall et al. |
| 2005/0238412 A1 | 10/2005 | Jacobs et al. |
| 2007/0154863 A1* | 7/2007 | Cai et al. ................... 433/89 |
| 2007/0166663 A1 | 7/2007 | Telles et al. |

(Continued)

FOREIGN PATENT DOCUMENTS

| | | |
|---|---|---|
| DE | 2526640 | 12/1976 |
| DE | 102004057737 | 3/2006 |

(Continued)

OTHER PUBLICATIONS

Reynolds, Contents of toothpaste—safety implications, Australian Prescriber, Apr. 1994, vol. 17(2),49-51, printed from http://m.australianprescriber.com/magazine/18/1/4/7/letters/38/contents-of-toothpaste#/magazine/17/2/49/51/, 5 pages.*

(Continued)

*Primary Examiner* — Gigi Huang

(57) ABSTRACT

An oral care implement includes a head (12), a handle (10), a neck portion (11) connecting the head and the handle, and a reservoir (15) located in the neck portion which contains at least one active agent. The implement has an activator (22) for activating a delivery device which delivers the active agent to one or more outlets (50). A wide variety of types of active agents may be administered at appropriate and accurate doses for therapeutic, hygienic, and/or other benefit.

8 Claims, 2 Drawing Sheets

(56) References Cited

U.S. PATENT DOCUMENTS

2008/0118300 A1* 5/2008 Burrowes ................ 401/270
2009/0263176 A1* 10/2009 Mileti et al. ................ 401/184

FOREIGN PATENT DOCUMENTS

| RU | 2048135 | 11/1995 |
| RU | 2108053 | 4/1998 |
| WO | WO 00/15076 | 3/2000 |
| WO | WO 02/058508 | 8/2002 |
| WO | WO 2006/100627 | 9/2006 |
| WO | WO 2007/008908 | 1/2007 |
| WO | WO 2007/073917 | 7/2007 |

OTHER PUBLICATIONS

International Search Report and Written Opinion of the International Searching Authority [EP] for corresponding International Application No. PCT/US2008/064630 mailed Apr. 15, 2009.

International Search Report and Written Opinion of the International Searching Authority [EP]for International Application No. PCT/US2008/066828 mailed Feb. 26, 2009.

* cited by examiner

ACTIVE DELIVERY ORAL CARE IMPLEMENT

BACKGROUND OF THE INVENTION

The present invention is directed to an oral care implement including a delivery system for a fluid. Oral care implements, particularly toothbrushes, are typically used by applying toothpaste to a bristle section followed by brushing regions of the oral cavity, e.g., the teeth, tongue, and/or gums. Some toothbrushes have been equipped with fluid reservoirs and systems for delivering auxiliary active agents, such as whitening agents, breath freshening agents, and the like.

Some efforts have been made to configure toothbrushes to deliver active agents at the time of brushing. Commonly assigned U.S. 2007/0154863 A1, for example, describes an oral care implement having a reservoir containing an active agent and a user-activated pump for delivering the active agent through a channel and out of one or more outlets.

BRIEF SUMMARY OF THE INVENTION

An oral care implement has a head, a handle, a relatively narrow neck portion connecting the head and the handle, and a reservoir located in the neck portion which contains at least one active agent. The implement has a delivery device actuator, such as a switch, for activating a delivery device, such as a pump, which delivers a predetermined amount of a substance, such as an active agent, to one or more outlets, which may be located in the vicinity the tooth cleaning elements, e.g., bristles, and/or other portion(s) of the oral care implement. A wide variety of active agents may be administered for therapeutic, hygienic, and/or other benefits, such as fresh breath, tooth whitening, reducing sensitivity of the teeth or producing sensations of heat, cool, or tingling.

The oral care implement advantageously may be manufactured at relatively low cost, is easy to use, and may deliver a medium through one or more outlets upon a user activating a switch. By locating a reservoir in the neck portion, the distance that the medium is dispensed to the head is minimized. This way the implement is less prone to clogging, the required volume of the reservoir may be reduced, and the reservoir may be more easily replaced for changing or replenishment of the active agent.

DETAILED DESCRIPTION OF THE INVENTION

Figure 1:
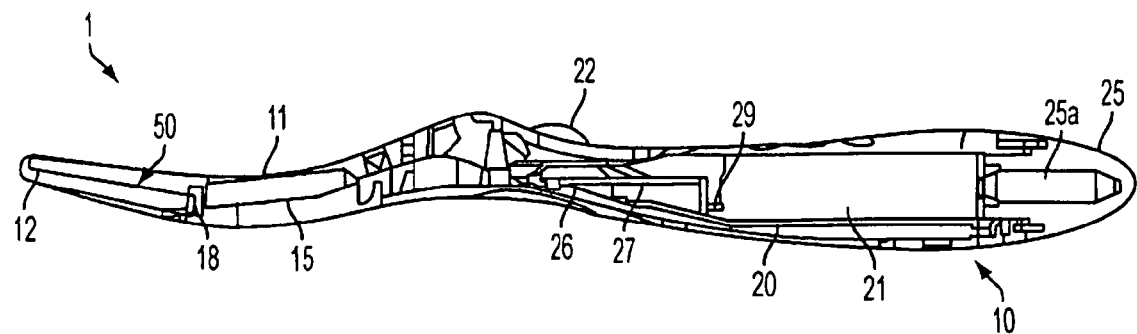
FIG. 1 is a side elevation view of a toothbrush having an active agent pump delivery system in a neck portion.

FIG. 1 schematically illustrates a toothbrush 1 having a handle 10, a head 12, and a relatively narrow neck portion 11 connecting the handle 10 and head 12. The head contains tooth cleaning elements, such as bristles and/or elastomeric cleaning elements (not shown) or the like. A reservoir 15 is provided within the neck portion 11 for storing a medium which may contain an active agent. The handle 10 or other exterior portion of the toothbrush 1 may contain a delivery device actuator or switch, such as a user-actuated button 22, for activating a delivery device, such as a pump 18. The pump 18 may be located upstream or downstream of the reservoir 15. As discussed below with reference to FIG. 2, in one aspect the reservoir 15 may be integrated with a pump 18'. Upon pressing the button 22, the pump 18 causes the medium to be delivered from the reservoir 15 to one or more outlets 50 located on the head 12. The outlets 50 may be located on the surface of the head 12 between or in the vicinity of the bristles or on other portions of the head 12. For example, outlets 50 may be spaced along the length of the bristle section to help disperse the medium throughout the bristle field. The active agent alternatively may be delivered through the bristles if the bristles comprised hollow lumens or the like. The active agent may also be delivered simultaneously through outlets 50 located at different portions of the toothbrush 1, for example to aid in the application of the active agent to different areas of the mouth. Optionally, a plurality of outlets may be provided on both the surface of the head that contains the tooth cleaning elements as well as the opposite the surface of the head, e.g., for delivering the same active agent from a common supply or different active agents from separate supplies. Although reference is made to a plurality of outlets, it is contemplated that a single outlet could be used.

The switch for activating the pump 18 may be a button 22, as illustrated in FIG. 1, or may be another type of switch such as a user-activated toggle switch or rotating dial. Depressing the button 22 may activate a timing circuit which causes the pump 18 to operate for an interval needed to pump a predetermined amount of the medium containing the active agent from the reservoir 15 and through the outlets 50. The pump has a power source, such as a battery 21, which may be located in the handle portion 10. The timing circuit causes the pump 18 to operate for an interval of time which either may be preset or may be adjustable, e.g., by a user-activated rotating dial, which may vary depending on the active agent and the desired delivery regimen. While an external switch 22 has been described, it will be appreciated that a user-operated, internal switch that activates the delivery device upon the mechanical action of brushing, is also contemplated.

The medium containing the active agent may be incorporated into a sealed reservoir 15 during manufacture of the toothbrush 1, in which case the toothbrush 1 may be disposed of after the supply of the active agent is exhausted. Alternatively, the reservoir 15 may be refillable through an inlet (not shown), or may be replaceable, e.g., by inserting a replaceable cartridge into a recess in the toothbrush. A cartridge may be provided with a sharpened element which penetrates a membrane in the recess to permit the medium to flow from the cartridge. The cartridge may be spring-loaded to stay in place after insertion into the recess, and can have a seal to prevent unwanted leakage of the active agent. The cartridge may be disposable or refillable. Other methods of providing a refillable and/or replaceable cartridge or the like may be used.

The reservoir 15 and pump 18 may be fixed to the neck portion 11 by various known methods including bonding, molding, melting, and mechanical fixing.

Optionally, a user-activated switch, such as a dial (not shown), can have multiple settings for selecting one of several active agents. For example, the dial can have a first setting for oxidizer/whitener treatment, a second setting for breath freshener treatment, and a third setting for antimicrobial treatment. The dial setting instructs the timing circuit to activate the pump 18 for a time interval appropriate for the selected active agent.

In one embodiment, a kit comprises a toothbrush and at least one cartridge containing an active agent. A user may select among multiple cartridges for a desired treatment. If the active agents have different intervals of application, the toothbrush may be provided with a dial, as previously described, to enable the user to select the appropriate setting. Similarly, a single cartridge can come pre-loaded with multiple active agents that may be selectively accessed and delivered by a switch or the like. The kit can also include a dentifrice if desired.

The active agent may be delivered in a dose appropriate for its intended purpose. The amount may be controlled by controlling the duration the pump 18 operates after the button 22 is pressed. The duration of dispensation will depend on the desired dose and the flowrate of the medium, and typically ranges from about 1 second to 5 minutes, often from about 5 seconds to about 2 minutes, and may range from about 10 seconds to 30 seconds. The timing of the dispensing action may be either immediately after the button 22 is pressed, or at a delay programmed as desired.

Any suitable pump may be used for delivering the medium from the reservoir 15 to the outlet(s). The pump may deliver the medium through a variety of different actions that are mechanical, electrical, chemical or a combination thereof, depending on the pump structure.

Figure 2:
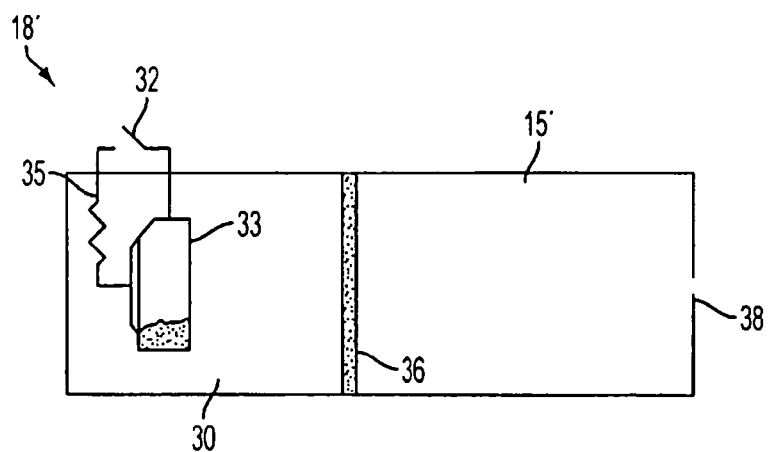
FIG. 2 schematically illustrates a pump system.

FIG. 2 is a schematic illustration of a pump 18' with an integrated reservoir 15 which may contain the medium. The pump 18' has a pressure side 30 which houses a pump device 33 that is activatable by an activation switch 32. The pump device 33 is integrated into a circuit which includes a resistor 35 and a power source (not shown). When the pumping 33 is activated by the switch, the internal pressure on the pressure side 30 is increased, which displaces a piston 36 toward the reservoir 15', which in turn causes the medium to be dispensed through an orifice 38.

Figure 3:
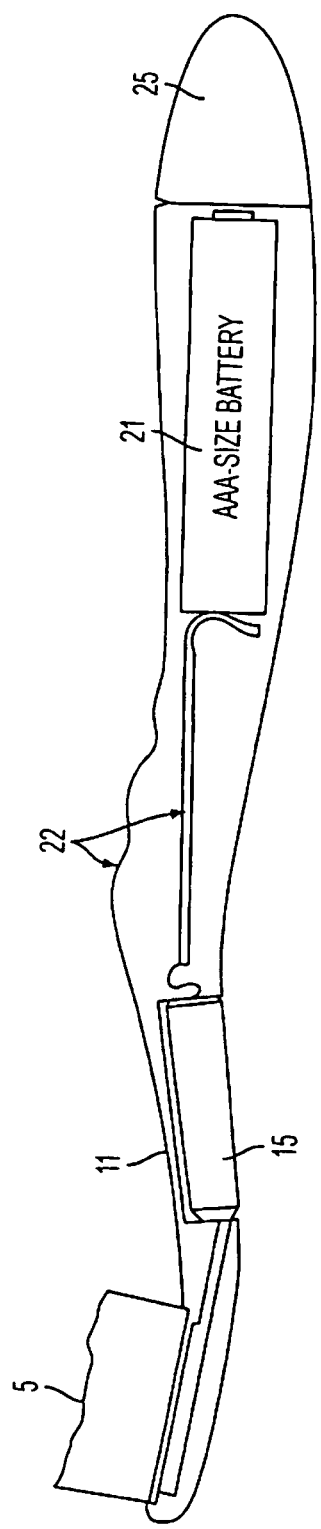
FIG. 3 is a side elevation view of an alternative toothbrush having an active agent pump delivery system in a neck portion.
Figure 4:
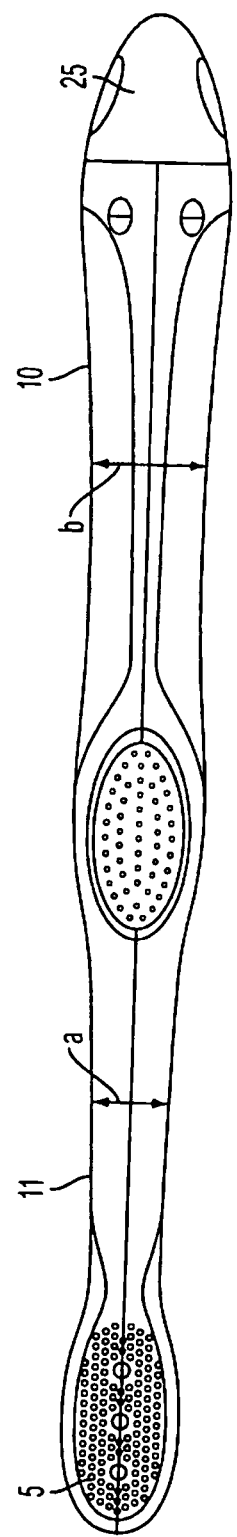
FIG. 4 is a top plan view of the toothbrush of FIG. 3.

FIGS. 3 and 4 show an alternative construction in which the reservoir 15 is positioned at the bottom of the neck portion 11. A relatively short (e.g., about 10-20 mm) channel connects the reservoir 15 to outlet(s) located in the head portion. An external pump may be provided, which creates negative pressure to pull the medium from the reservoir 15.

With reference to FIG. 4, the cross-sectional area "b" of the handle portion 10 may be suitably selected to provide sufficient storage space for the battery 21, such as an AAA type, or button type battery or other generally cylindrical battery, while also providing ergonomic characteristics to permit easy gripping and manipulating of the toothbrush. The neck portion 11 has a cross-sectional area "a" which is generally less than that of the handle portion 10 and may be suitably selected to provide sufficient storage space for the reservoir 15. Either or both of the neck portion 11 and handle portion 10 may have contours such that the respective cross sectional areas ("a" and/or "b") is non-uniform. Given these considerations, the ratio of the average cross-sectional area of the handle portion "b" to the average cross-sectional area of the neck portion "a" usually satisfies the relationship $1<b/a\leq5$, and often $1.2\leq b/a\leq4$. Nevertheless, other values of the ratio are possible.

Advantageously, by locating the reservoir 15 in the neck portion 11, the distance that the medium is dispensed to the head 12 is minimized. The length of the channel used for delivering the medium from the reservoir 15 to the head 12 may range, for example, from about 10 to 20 mm. In this way the implement is less prone to clogging, the required volume of the reservoir 15 may be reduced, and the reservoir 15 may be more easily replaced for changing or replenishment of the active agent.

The active agent itself may be contained in the reservoir 15. In other words, it is not necessary to generate the active agent internally or in situ. This simplifies the construction of the toothbrush and avoids the need to handle any byproducts associated with the synthesis of the active agent. Alternatively, an agent in one reservoir may be delivered via a delivery device to another reservoir where it is "activated," where it is then delivered via another delivery device to the one or more outlets. A delivery system may employ multiple connections that are direct or indirect.

In FIGS. 1 and 3-6, a toothbrush 1 is shown schematically having a head 12, a relatively narrow neck portion 11, and a handle 10. Any bristle configuration and any handle configuration may be used. The outlet(s) may be located in the bristle region on the bristle side of the head of the toothbrush, for example between or interspersed with bristles. Alternatively, the outlet(s) may be located on the side of the head opposite the bristles, or on the side edges of the head 12, or on a combination of sides as desired. Alternatively, the outlet(s) may be located adjacent the head 12 or in the region of the head 12, but not actually on the head 12.

The toothbrush 1 may be used by applying toothpaste to the bristles and brushing the teeth in a conventional manner. The active agent may be administered by activating the switch, e.g., depressing button 22, to activate the pump 18, which causes the medium containing the active agent to be delivered though the outlet(s). The switch may instruct the timing circuit to activate the pump 18 for a predetermined time, which in turn dispenses the active agent in a predetermined amount. Alternatively, the active agent may be administered in a user-defined amount, for example, dispensation may occur for the duration that the button 22 is depressed. The active agent may then be applied to the teeth using the bristles. The active agent may be administered before, during, or after brushing.

Non-limiting examples of active agents which can be used include antibacterial agents, such as chlorhexidine, cetyl pyridininum chloride, triclosan, stannous compounds, herbal extracts and zinc compounds; oxidative or whitening agents, such as hydrogen peroxide, urea peroxide, sodium percarbonate, and PVP—$H_2O_2$; supercharged fluoride delivery ingredients (such as dicalcium phosphate dihydrate and others disclosed in U.S. Pat. No. 5,785,956); tooth sensitivity ingredients, such as $KNO_3$; occluding agents, such as Novamin® bioactive glass, sodium silicate, and arginine salts such as arginine bicarbonate; gum health actives, including those which reduce inflammation pathways and/or interfere in bacterial processes which produce inflammatory stimuli, such as polyphenols (such as baicalin and catechin), herbal extracts and triclosan; nutritional type ingredients, such as vitamins, minerals, amino acids, vitamin E, and folic acid; tartar control or anti-stain ingredients, including phosphate salts, polyvinylphosphonic acid, PVM/MA copolymer; enzymes, such as those used for plaque disruption; sensate ingredients, such as those providing cooling, tingle, or heat sensations; flavors and flavor ingredients; anti-cavity or enamel repair agents; breath freshening ingredients; oral malodor reducing agents; anti-attachment agents, such as ethyl lauroyl arginate and silicone polymers; diagnostic solutions, such as plaque-indicator dyes; colorants or other aesthetic agents; and combinations thereof. Examples of flavors and flavor ingredients include essential oils, menthol, carvone, and anethole, and various flavoring aldehydes, esters, and alcohols. Examples of essential oils include oils of spearmint, peppermint, wintergreen, sassafras, clove, sage, eucalyptus, marjoram, cinnamon, lemon, lime, grapefruit, and orange.

The active agent and/or its medium can be selected to complement a toothpaste formula, such as by coordinating flavors, colors, aesthetics, or active ingredients. A flavor can be administered to create a gradual flavor change during brushing, which presently is not possible using toothpaste alone.

The active agent may be compatible with toothpaste, or may be unstable and/or reactive with typical toothpaste ingredients. Non-limiting examples of components which tend to be unstable and/or reactive with typical toothpaste ingredients include hydrogen peroxide, sodium fluoride, various calcium salts, cetyl pyridinium chloride, ethyl lauroyl arginate, silicone polymers, enzymes, and chlorhexidiene. The active agent also may be a tooth cleaning agent to boost the overall efficacy of brushing. Such tooth cleaning agents may or may not be compatible with the toothpaste ingredients.

The active agent can be provided in any suitable vehicle, such as in aqueous solution or in the form of gel or paste; or in the form of a gas. In one example of an implementation, oxygen can aid in oxidation processes such as tooth whitening or air to enhance whole mouth flavor sensation. The use of air can increase the rate of diffusion of the flavor in the mouth. Non-limiting examples of vehicles include water, monohydric alcohols such as ethanol, poly(ethylene oxides) such as polyethylene glycols such as PEG 2M, 5M, 7M, 14M, 23M, 45M, and 90M available from Union Carbide, carboxymethylene polymers such as Carbopol® 934 and 974 available from B.F. Goodrich, and combinations thereof. The selection of a suitable vehicle will be apparent to persons skilled in the art depending on such factors as the properties of the active agent and the desired properties of the medium, such as viscosity.

The quantity of the medium dispensed may vary over a wide range depending on such factors as the identity of the active agent and its concentration in the medium. The quantity usually ranges from about 1 to about 500 µL per use, more usually from about 10 to about 100 µL. For example, the pump 18 may be configured to deliver 10 µL of 20% cetylpyridinium chloride gel over a period of 30 seconds, e.g., for application during the first 30 seconds of brushing the teeth. An advantage of this delivery is that ingredients incompatible with the toothpaste are exposed to the toothpaste as little as possible.

The reservoir 15 may contain a quantity of the active agent medium intended for a single use or a small number of uses, or may facilitate repeated use over an extended period of time, e.g., up to several months or several years (if used with a toothbrush having a replaceable head for example). The size of the reservoir 15 may be selected to be compatible with the desired overall dimensions of the toothbrush 1, particularly the neck portion 11, as well as such factors as the stability of the active agent and the quantity of medium administered during each application.

The supply of active agent in the reservoir 15 may be free or substantially free of components which are incompatible with the active agent and/or the medium containing the active agent, such as incompatible toothpaste components as previously identified. In one aspect, the reservoir 15 may be free or substantially free of toothpaste, as toothpaste is separately applied to the bristles by the user. Alternatively as noted above, an active agent may be originally retained in one reservoir and then transferred to another reservoir where it is activated just prior to delivery, which may be useful in certain conditions or circumstances.

The back of the toothbrush 1 may be equipped with a special surface for polishing teeth, for example, with silica toothpaste. Non-limiting examples of such surfaces include rubber, elastomer, woven fabric, and wool.

The toothbrush 1 optionally may be provided with compartments and/or access panels for access to the various components, such as the power source and reservoir. The power source may be, for example, a replaceable or rechargeable battery.

As illustrated in FIG. 1, the handle 10 may include a sheath or sleeve 20 which extends in the longitudinal direction of the handle 10 and is made of electrically conductive material. Both the handle 10 and the sleeve 20 are open to the rear, thus forming a cavity which can be closed from the rear by a threaded closure part 25. The battery 21 may be a commercially available, non-rechargeable cylindrical battery, with a defined power, e.g. 1.5 V. Alternatively, a button cell or rechargeable storage battery could be used as a power source.

A spring contact 29 for the positive pole of the battery 21 (see FIG. 1) is fitted in the sleeve 20, on a transverse wall, and is connected to the pump 18 via an electric line 26. The electrical connection can be interrupted by means of the switch 22.

The closure part 25 may be provided with a threaded stub 25a made of an electrically conductive material and can be screwed into the handle 1 and/or into the sleeve 20. The threaded stub 25a may be provided with a contact surface which, with the closure part 25 screwed in, comes into abutment against the negative pole of the battery 21 inserted into the sleeve 20. The negative pole is electrically connected to the pump 18 via the threaded stub 25a, the sleeve 20 itself, and a line 27 which connects the sleeve 20 to the pump 18. Instead of being transmitted via the electrically conductive sleeve 20, it would also be possible for the power from the negative pole to be transmitted in some other way, for example using wires or an electrically conductive plastic.

The following examples are provided for illustrative purposes and should be construed as illustrative and not limiting.

EXAMPLE 1

Table I illustrates a cetylpyridinium chloride concentrate that may be dispensed from a toothbrush reservoir during brushing as an antibacterial agent.

TABLE I

| Ingredient | Wt % |
|---|---|
| Carbopol 974P | 1-2 |
| PEG 600 | 10 |
| FD&C blue #1(1% solution in water) | 0.5 |
| Cetylpyridinium chloride | 20 |
| Water | Q.S. |

EXAMPLE 2

Table II shows a hydrogen peroxide solution that may be dispensed from a toothbrush reservoir during brushing as a whitening booster.

TABLE II

| Ingredient | Wt % |
|---|---|
| Carbopol 974P | 1-2 |
| Hydrogen peroxide | 30 |
| Water | Q.S. |

EXAMPLE 3

Table III illustrates a hydrogen peroxide gel that may be dispensed from a toothbrush reservoir during brushing as a whitening liquid. The gel also may be applied post-brushing for tooth whitening.

TABLE III

| Ingredient | Wt % |
| --- | --- |
| Water | 10.07 |
| Carbopol 974 | 1.00 |
| 95% Ethyl alcohol | 34.8 |
| Glycerin | 5.00 |
| PEG 600 | 10.00 |
| PEG 2M | 14.00 |
| Hydrogen peroxide | 25.00 |
| 85% Phosphoric acid | 0.05 |
| Monobasic sodium phosphate | 0.05 |
| Total | 100.00 |

EXAMPLE 4

Table IV shows a phosphoric acid solution that may be dispensed from a toothbrush reservoir during brushing as a whitening liquid. The solution has a pH of about 4.0.

TABLE IV

| Ingredient | Wt % |
| --- | --- |
| Purified water | 25.1 |
| Carbopol 974 | 1.00 |
| 95% Ethyl alcohol | 34.8 |
| Glycerin | 5.00 |
| PEG 2M | 15.00 |
| Urea peroxide | 18.00 |
| 85% Phosphoric acid | 0.10 |
| Monobasic sodium phosphate | 1.0 |
| Total | 100.00 |

EXAMPLE 5

Table V illustrates another hydrogen peroxide solution that may be dispensed from a toothbrush reservoir during brushing as a whitening booster. The composition alternatively may be applied to the teeth after brushing as a whitening agent.

TABLE V

| Ingredient | Wt % |
| --- | --- |
| Carbopol 974P | 1 |
| 95% ethyl alcohol | 34.8 |
| Glycerin | 5 |
| PEG 600 | 10 |
| PEG 2M | 14 |
| 85% phosphoric acid | 0.05 |
| Monobasic sodium phosphate | 0.05 |
| Hydrogen peroxide | 25 |
| Water | Q.S. |

EXAMPLE 6

Alternative liquid whitening gels are prepared by modifying the base formula of Example 5 by adding either (1) 2 to 5 wt % polyethylene (PE) powder having an average particle size of 6 to 8 microns; (2) 1 to 5 wt % polytetrafluoroethylene (PTFE) powder having particle size of 5 to 6 microns; (3) 0.8 to 2.5 wt % polypropylene (PP) powder having a particle size of 4 to 50 microns; (4) 2 to 5 wt % PE powder and 0.11 to 0.4 wt % titanium dioxide powder having a particle size of 10 to 45 microns. Examples of gels having the polymer and/or inorganic titanium powders incorporated in the base formula are shown in Tables VI and VII.

TABLE VI

| | A (wt %) | B (wt %) | C (wt %) | D (wt %) | E (wt %) | F (wt %) | G (wt %) |
| --- | --- | --- | --- | --- | --- | --- | --- |
| Base Formula | 99.0 | 98.0 | 95.0 | 98.0 | 95.0 | 99.2 | 97.5 |
| +PE | — | — | — | 2.0 | 5.0 | — | — |
| +PTFE | 1.00 | 2.0 | 5.0 | — | — | — | — |
| +PP | — | — | — | — | — | 0.8 | 2.5 |

TABLE VII

| | GA (wt %) | H (wt %) | I (wt %) | J (wt %) | K (wt %) | L (wt %) |
| --- | --- | --- | --- | --- | --- | --- |
| Base Formula | 99.5 | 97.90 | 97.80 | 97.60 | 94.90 | 99.5 |
| +PE | — | 2.00 | 2.00 | 2.00 | 5.00 | — |
| +TiO$_2$ | — | 0.10 | 0.20 | 0.40 | 0.10 | 0.5 |
| +TiO$_2$ coated mica | 0.5 | — | — | — | — | — |

EXAMPLE 7

Table VIII shows another exemplary composition of a liquid whitening gel that may be dispensed from a reservoir of a toothbrush during brushing as described herein.

TABLE VIII

| Liquid Gel Formula | Wt % |
| --- | --- |
| Carbomer | 1.00 |
| PEG 600 | 9.96 |
| BHT | 0.03 |
| Glycerin | 4.98 |
| Water | 17.00 |
| Ethyl alcohol | 34.67 |
| PEG 2M | 13.95 |
| H$_2$O$_2$ (35%) | 17.93 |
| Sodium Phosphate | 0.05 |
| Phosphoric acid | 0.05 |
| Titanium dioxide | 0.38 |

EXAMPLE 8

Table IX example shows the composition of a breath protection gel that is dispensed from a toothbrush reservoir as described herein.

TABLE IX

| Ingredient | Wt % |
| --- | --- |
| Carbopol 974P | 1 |
| PVM/MA copolymer | 10 |
| Triclosan | 20 |
| Ethyl alcohol | 40 |
| Zinc gluconate | 20 |
| Water | Q.S. |

What is claimed is:
1. An oral care implement comprising:
a head;
a handle;
a neck portion connecting the head and the handle, the neck portion having a front surface and a rear surface, the rear surface of the neck portion comprising a recess;

a replaceable cartridge comprising a pump and an integrated reservoir which contains at least one active agent, the replaceable cartridge positioned within the recess;

at least one outlet; and wherein activation of the pump delivers the active agent from the reservoir to the at least one outlet.

2. The oral care implement of claim 1, wherein the head includes tooth cleaning elements and wherein the at least one outlet comprises a plurality of outlets in the vicinity of the tooth cleaning elements.

3. The oral care implement of claim 1, wherein the active agent is selected from the group consisting of antibacterial agents; oxidative or whitening agents; enamel strengthening or repair agents; tooth erosion preventing agents; tooth sensitivity ingredients; gum health actives; nutritional ingredients; tartar control or anti-stain ingredients; enzymes; sensate ingredients; flavors or flavor ingredients; breath freshening ingredients; oral malodor reducing agents; anti-attachment agents or sealants; diagnostic solutions; occluding agents, dry mouth relief ingredients; catalysts to enhance the activity of any of these agents; colorants or aesthetic ingredients; and combinations thereof.

4. The oral care implement of claim 3, wherein the active agent is selected from the group consisting of (i) an antibacterial agent selected from the group consisting of chlorhexidine, cetyl pyridinium chloride, triclosan, stannous compounds, herbal extracts, and zinc compounds; (ii) an oxidizing or whitening agent selected from the group consisting of hydrogen peroxide, urea peroxide, sodium percarbonate, and polyvinylpyrrolidone-hydrogen peroxide (PVP-$H_2O_2$); (iii) a gum health active selected from the group consisting of polyphenols, herbal extracts, and triclosan; (iv) a nutritional ingredient selected from the group consisting of vitamins, minerals, amino acids, vitamin E, and folic acid; (v) tartar control or anti-stain agent selected from the group consisting of phosphate salts, polyvinylphosphonic acid, and a copolymer of methyl vinyl ether and maleic anhydride (PVM/MA copolymer) (vi) a flavor or flavor ingredient selected from the group consisting of menthol, carvone, anethole, aldehydes, esters, alcohols, and oils of spearmint, peppermint, wintergreen, sassafras, clove, sage, eucalyptus, marjoram, cinnamon, lemon, lime, grapefruit, or orange; (vii) an occluding agent selected from the group consisting of sodium silicate, bioactive glass and arginine salts; (viii) an anti-attachment agent selected from the group consisting of ethyl lauroyl arginate and silicone polymers; and (ix) combinations thereof.

5. The oral care implement of claim 1, wherein the reservoir contains a plurality of active agents, and further comprising an adjustable switch to select one of the plurality of active agents for delivery to the at least one outlet.

6. The oral care implement of claim 5, wherein the adjustable switch is a dial.

7. The oral care implement of claim 1, wherein the reservoir further comprises a plurality of active agents selectively deliverable to the at least one outlet.

8. The oral care implement of claim 1, wherein a power source for the pump is located in the handle.

* * * * *